United States Patent [19]

Foster

[11] Patent Number: 5,575,765
[45] Date of Patent: Nov. 19, 1996

[54] TRACTION APPARATUS AND METHOD

[76] Inventor: Steven K. Foster, 1825-36th Avenue Ct., Greeley, Colo. 80634

[21] Appl. No.: 579,206

[22] Filed: Dec. 28, 1995

[51] Int. Cl.[6] .................................................. A61F 5/00
[52] U.S. Cl. ........................................... 602/32; 606/241
[58] Field of Search ......................... 602/32–36, 38–40, 602/19; 606/237, 240–241

[56] References Cited

U.S. PATENT DOCUMENTS

| 913,127 | 2/1909 | Haas | 602/32 |
|---|---|---|---|
| 1,347,913 | 7/1920 | Rink | 602/32 X |
| 2,488,058 | 11/1949 | Fleishman | 602/39 |
| 4,114,611 | 9/1978 | Lyle et al. | 602/32 X |
| 4,951,654 | 8/1990 | Gambale et al. | |
| 5,129,881 | 7/1992 | Pope | |
| 5,192,305 | 3/1993 | Sastre | 606/241 |

FOREIGN PATENT DOCUMENTS

| 1114413 | 9/1984 | U.S.S.R. | 602/39 |
|---|---|---|---|
| 1517958 | 10/1989 | U.S.S.R. | 606/241 |

OTHER PUBLICATIONS

Donald K. Harrison, M.S., D.C., *Spinal Biomechanics: A Chiropractic Perspective*, Chapters 3 & 25 (1992).

Primary Examiner—Stephen R. Crow
Assistant Examiner—David R. Risley
Attorney, Agent, or Firm—William E. Hein

[57] ABSTRACT

A traction apparatus and method for remodeling a human subject's spinal posture toward an ideal normal static spinal model includes a rectangular frame within which the subject is supported on a knee rest and a pelvic rest. A traction belt is placed around the subject's pelvis from behind and anchored to a rear vertical column of the frame. A shoulder harness is applied from behind and also anchored in the same manner. A traction belt is placed around the dorsolumbar region from the front, and secured to a front vertical column of the frame. A rigid curved fulcrum is placed behind the cervical spine from the front and secured to the front column, either directly or via a pulley mounted on a horizontal toprail of the frame. A head halter is applied over the forehead and under the chin from behind and is secured to the rear vertical column, either directly or via a pulley mounted on the horizontal toprail of the frame. An occipital sling is placed underneath the occiput and secured to the front vertical column of the frame via a pulley mounted on the horizontal toprail. Adequate tension is applied to the pelvic and dorsolumbar belts, shoulder harness, cervical fulcrum, head halter, and occipital sling as necessary to achieve the desired rheologic effect.

14 Claims, 2 Drawing Sheets

TRACTION APPARATUS AND METHOD

BACKGROUND AND SUMMARY OF THE INVENTION

This invention relates generally to traction systems and more particularly to a traction apparatus that is capable of applying traction forces simultaneously to selected areas of the human spine for the purpose of remodeling spinal posture toward an ideal normal static spinal model.

The ideal normal static spinal model can be characterized by two main criteria. The first of these criteria requires vertical alignment of all of the vertebral centers of mass over the lower limb centers of mass. This means that the skull center of mass, the thoracic center of mass, the pelvic center of mass, the mid-knee, and the mid-ankle are all vertically aligned in both the frontal and median planes. The second of these criteria requires that the primary (kyphotic) and secondary (lordotic) spinal curvatures, as viewed in the median plane, subtend a circular arc of sixty-three degrees.

Abnormal human spinal postures can be categorized as translations and/or rotations of the skull, thorax, or pelvis relative to the immediately inferior center of mass in a 3-dimensional Cartesian coordinate system. Abnormal postures defined in this manner would therefore consist of positive/negative translations along the x, y, z axes or positive/negative rotations about these axes. An abnormal posture could be as simple as a single deviation along or about one axis for one center of mass or as complex as to involve six degrees of freedom for each center of mass relative to the one below.

Spinal degenerative disease, particularly disc disease, is always promoted and often initiated by the alteration of spinal posture from the ideal. As postural alignment departs from the ideal, the transmission of force through the spine is altered, and damaging forces are applied into localized regions of the spine. These areas gradually deteriorate and decline in function and integrity. The resultant spinal instability leads to symptoms and disability. Therefore, any method and apparatus that can effectively correct spinal postural abnormalities is of great benefit to mankind.

The known application of traction forces to the human spine dates back to the time of Hippocrates. However, the greatest portion of study and development in this field has been completed within the last fifty years. With few exceptions, spinal traction has consisted of axially applied forces, most often to address such clinical entities as fracture, dislocation, radicular pain, or spondylosis.

It is only recently that a field of study has developed that entails the use of traction forces with the express purpose of remodeling spinal posture. To date, the most effective postural remodeling efforts are based on known rheologic principles and soft tissue deformation concepts. In practice, these principles dictate repetitive application of forces at sufficient amplitude, specific angle of incidence, and for sufficient time periods to exhaust elastic resistance and achieve the desired plastic deformation of the soft tissue elements being tractioned. The present invention allows the repetitive application of such controlled forces in the cervical, thoracic, and lumbar spine, as well as within the shoulder girdles and rib cage.

The use of traction for the purpose of correcting abnormal spinal postures has a limited history. The earliest attempts were efforts to correct scoliotic spinal curvatures. One such invention, known as the Von Lackum table, involved placing the subject flat on a table and applying forces to the subject by way of belts strapped around the torso and secured to either side of the table under tension.

Recent renewed interest in postural remodeling, particularly within the field of chiropractic, has led to advancement in this field. However, even though the basic principles of spinal postural remodeling are now clearly defined, the actual application has been limited and concentrated almost exclusively upon the cervical spinal lordotic posture. Exemplary of the prior art devices directed toward remodeling spinal posture are those described in U.S. Pat. Nos. 4,951,654 and 5,129,881. However, in these references, only passive forces of low amplitude, with little control over angle of incidence are applied below the cervical spine. The traction devices of the prior art are therefore limited in their ability to achieve spinal postural remodeling below the level of the cervical spine. In addition, both of these references produce an undesirable component of basilar compression at the antlanto-occipital region.

In U.S. Pat. No. 4,951,654 to Gambale et al., a subject reclines over an angled recumbent table with a harness placed across the forehead to exert a controlled compressive extension force to the cervical spine. No active forces are applied below the level of the forehead. Passive gravitational force is recruited by placing a fulcrum under the lower back.

In U.S. Pat. No. 5,129,881 to Pope, a subject is seated in a chair with lumbar and dorsal support. A harness is passed around the cervical spine from the front and anchored in front of the subject at a controlled angle and force. A second harness is applied to the forehead and around the lower back skull and placed under tension to exert an extension force to the cervical spine at a controlled angle and force. A fulcrum is applied between the chair and the subject at the lumbar spine, but no active force is applied below the cervical spine.

Other prior art methods of cervical traction with the intent of spinal postural remodeling include having the subject lie supine on a flat bench with a small fulcrum under the cervical spine and a harness attached to the chin and/or forehead to exert a force superiorly and/or posteriorly relative to the torso. Alternatively, the subject may be seated with the head tipped back and with a harness across the forehead attached to a weight pulling the head downward into forced extension.

Still other prior art methods of applying forces into the dorsolumbar spine for the purpose of spinal postural remodeling include exercises that are done in a supine posture while lying over a fulcrum at the mid-dorsal spine, or lying over a sling that is suspended from above, with the sling placement at the area of the dorsolumbar spine to be tractioned.

It is therefore a principal object of the present invention to provide a traction apparatus in which the subject to be tractioned is placed in a semi-upright posture that allows complete and easy access to the spine and axial skeleton from any direction for unrestricted traction setup. This position is nearly identical to the subject's natural upright standing posture from the pelvis up, thereby maintaining active proprioceptive input to the nervous system during traction application to thereby facilitate postural remodeling. This position is also the same as the one in which the ideal normal static spinal model is drawn, thereby allowing visual confirmation of correct traction positioning by simple comparison of the actual setup to the ideal.

It is a further object of the present invention to provide a traction apparatus that permits the application of traction forces, controllable both with respect to amplitude and angle of incidence, to be actively and directly applied to the pelvis, the dorsolumbar spine, each shoulder girdle, the cervical spine, and the head.

It is a further object of the present invention to provide a traction apparatus that provides extreme variability in the angle of incidence of traction forces. A cervical fulcrum can originate in any position within the median plane from in front of and below the subject to directly above the subject. A head halter can originate in any position within the median plane from below and behind the subject to above and in front of the subject. A pelvic traction belt, dorsolumbar traction belt, and shoulder harness can originate from below to above the point of subject contact within the median plane. In addition, by placing a block underneath one knee at the knee rest, rotation of the pelvis about the z-axis can be achieved, with compensatory z-axis rotational changes taking place throughout the spine. In the same manner, by placing wedges unilaterally within the traction belts, between the subject and the pelvic rest, or by applying asymmetrical tension to the shoulder harness, the subject can be rotated about the y-axis, thereby introducing a rotational component to the angle of incidence.

It is a further object of the present invention to provide a traction apparatus that includes a shoulder harness for providing a more stable base for cervical traction application. The shoulder harness allows placement of the shoulders in a retracted position to achieve more effective postural remodeling of the cervical spine, which anatomically extends to the second dorsal vertebra. In addition, forces can be directed into the thoracic spine and rib cage by using the shoulders as levers. Finally, traction forces can be directed into the shoulders themselves to address abnormal shoulder postures.

It is a further object of the present invention to provide a method of alleviating the basilar compression component at the atlanto-occipital region during cervical extension traction.

It is yet another object of the present invention to provide a traction apparatus that is capable of applying postural corrective traction forces to all areas of the spine, axial skeleton, and shoulder girdles at the same time. The concerted application of traction forces throughout the spine increases the effect of each local application by creating a corrected point of reference for local applications and by increasing the amplitude of the neurologic proprioceptive input that facilitates more rapid postural remodeling.

These and other incidental objects are accomplished in accordance with the illustrated preferred embodiment of the present invention by providing a traction apparatus including a frame, knee and pelvic rests within the frame for receiving the subject, a head halter, a cervical fulcrum, an occipital sling, a shoulder harness, a dorsolumbar traction belt, a pelvic traction belt, and associated tensioning devices operative for applying desired tractional forces to the spine and other anatomic contact points of the subject.

DETAILED DESCRIPTION OF THE INVENTION

Figure 1:
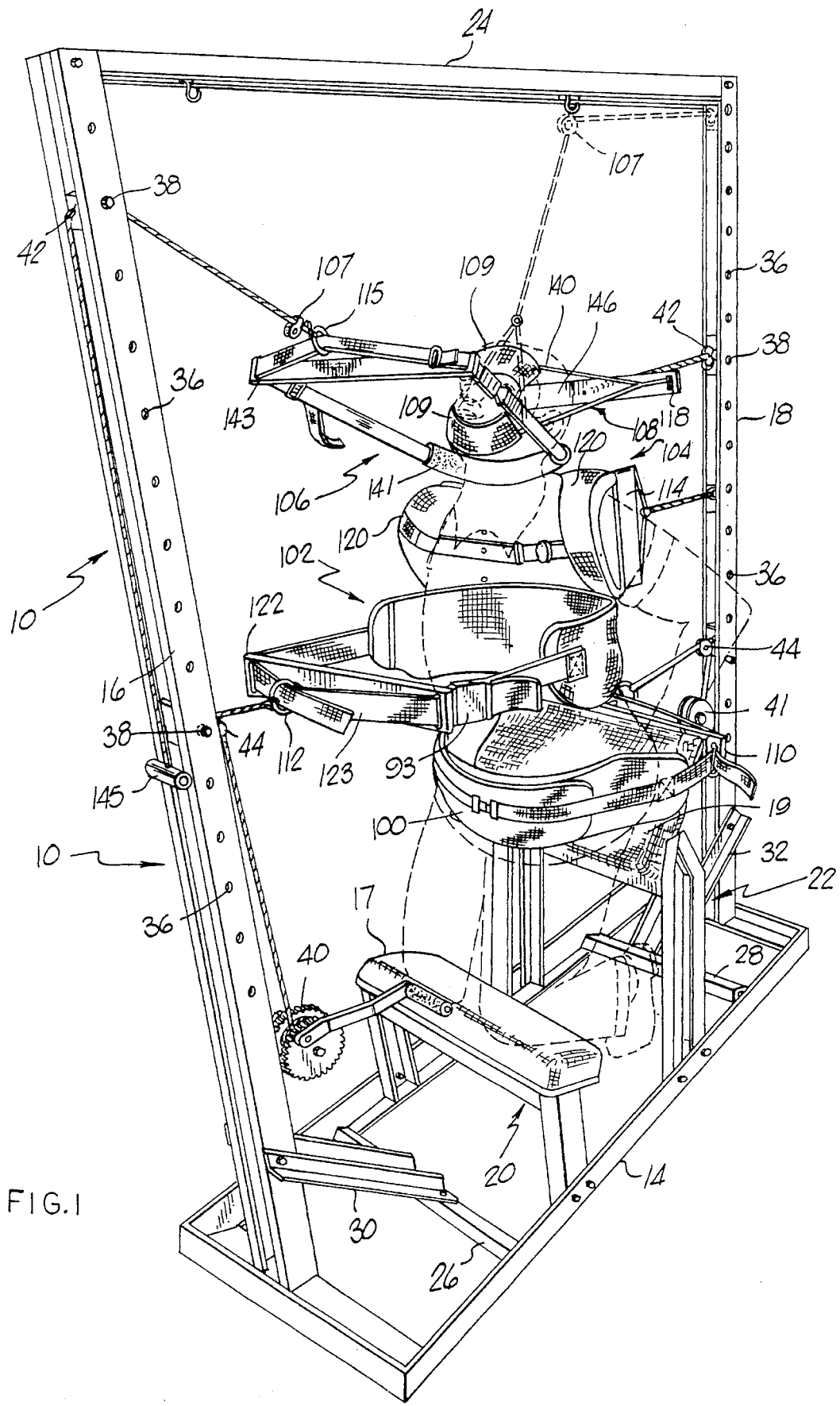
FIG. 1 is a perspective view of the traction apparatus of the present invention, illustrating a head halter, cervical fulcrum, occipital sling, shoulder harness, dorsolumbar traction belt, pelvic traction belt, and associated tensioning devices operative for applying desired tractional forces to the spine of a subject.
Figure 2:
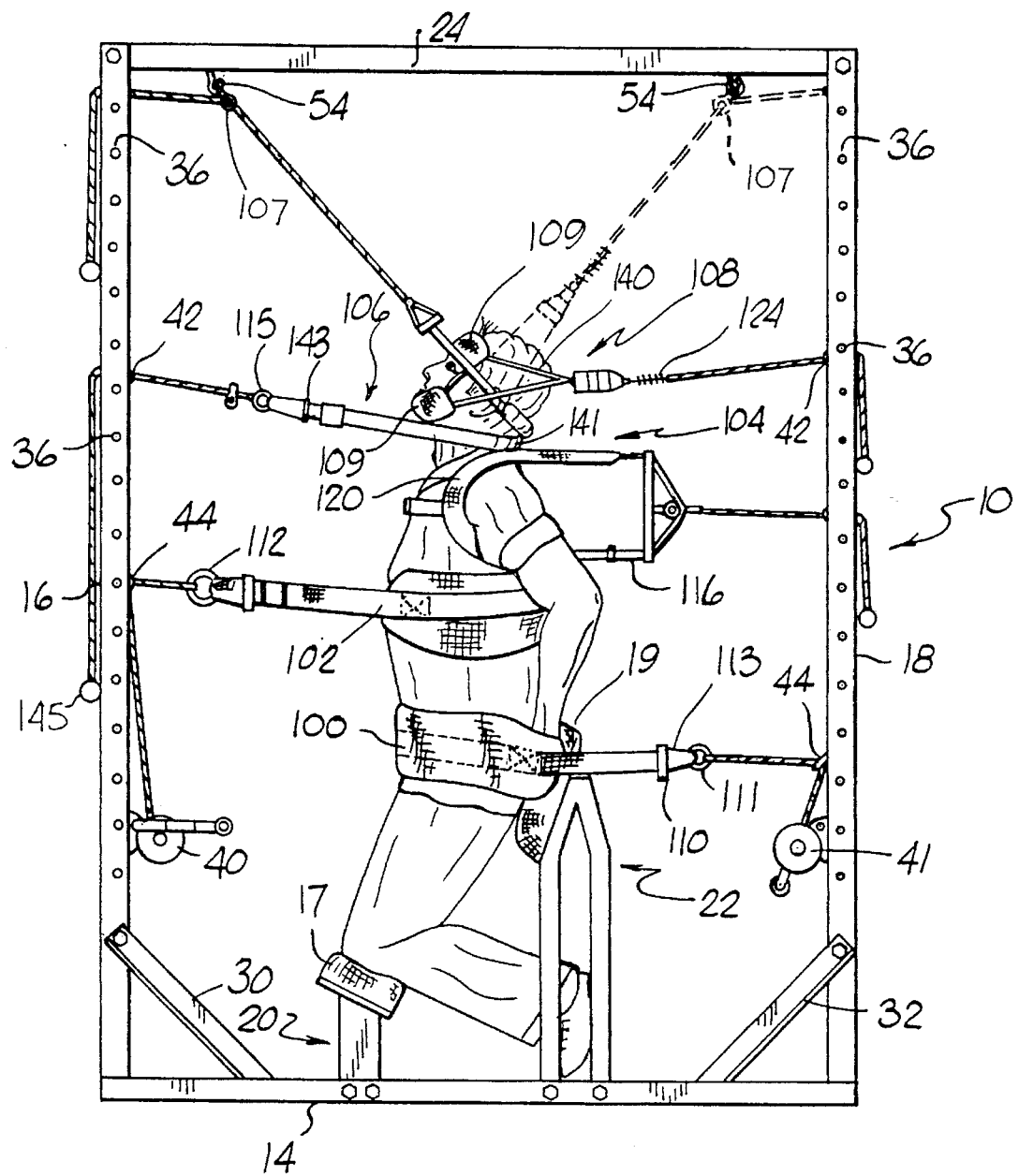
FIG. 2 is a side view of the traction apparatus of FIG. 1.

Referring now to FIGS. 1 and 2, there is shown a traction apparatus 10 that includes a frame having a rectangular base 14, an anterior vertical column 16, a posterior vertical column 18, a knee rest 20, a pelvic rest 22, and a toprail 24. The anterior vertical column 16 and the posterior vertical column 18 are rigidly attached at the midpoint along the front and rear aspects of the base 14, respectively. The toprail 24 connects the anterior and posterior vertical columns 16, 18 at their highest point. Additional support structure for the vertical columns 16, 18 is provided by crossbraces 26, 28 which rigidly connect the two sides of the base 14 near the front and rear thereof and column supports 30, 32 which rigidly connect the crossbraces 26, 28 and the vertical columns 16, 18. Knee rest 20 is rigidly attached to either side of the base 14 toward the front aspect and includes a knee pad 17, positioned at a slightly downward angle toward the rear of the apparatus, for comfortably receiving the knees of the subject. The pelvic rest 22 is similarly rigidly attached to either side of the base 14 toward the rear aspect and includes a pelvic pad 19, positioned at a downward angle toward the front of the apparatus, for comfortably receiving the pelvis of the subject.

The frame of traction apparatus 10 may be constructed using any of a number of conventional techniques, but welded frame construction has been found to be desirable. The anterior and posterior vertical columns 16, 18 are fabricated to be identical. Each comprises two pieces of opposed channel material rigidly joined at the top and bottom to maintain a separation between the opposing sides and a clear channel within. The vertical columns 16, 18 are positioned relative to the rectangular base 14 such that the separation is in line with the median plane of the long axis of the base 14. Each of the vertical columns 16, 18 includes a plurality of spaced holes 36 placed centrally at regular intervals along the length thereof for receiving locking pins 38 that pass through each of the vertical columns 16, 18 transversely.

The vertical columns 16, 18 receive cam-cleat assemblies 42 and pulley assemblies 44 within their channels. Each of the cam-cleat assemblies 42 comprises a commercially available cam-cleat and rope guide mounted on a small block that may comprise nylon or some other plastic type material, for example, and that is machined to travel smoothly up and down within the channel of the vertical columns 16, 18. A hole that passes centrally and transversely through the block accepts a locking pin 38 for locking each of the cam-cleat assemblies 42 into a desired position along the vertical columns 16, 18. The cam-cleat assemblies 42 are inserted into the channel within vertical columns 16, 18 such that ropes connected to a shoulder harness 104, a cervical fulcrum 106, a head halter 108, and an occipital sling 105 can be drawn through a corresponding one of the cam-cleat assemblies 42 away from the subject and releasably locked in a desired position. Each of the pulley assemblies 44 comprises a commercially available pulley mounted on a block identical to that employed in the cam-cleat assemblies 42. Each of the pulleys is mounted on the front surface of its associated block so that the pulley projects through the separation of the one of the vertical columns 16, 18 on which that pulley assembly is mounted, toward the subject.

A light duty winch 40 is mounted on the interior side of the vertical column 16, and a second light duty winch 41 is similarly mounted on the interior side of vertical column 18. Each of the winches 40, 41 is mounted at a position above the base 14 that is approximately one quarter of the height of the vertical columns 16, 18. Each of the winches 40, 41 is of a commercially available type having a gear ratio of approximately 3:1 and having a handcrank and locking mechanism. Winch 40 controls the tension on a rope that passes through a pulley assembly 44 and is connected to a dorsolumbar traction belt 102. Winch 41 similarly controls the tension on a rope that passes through another pulley assembly 44 and is connected to a pelvic traction belt 100.

Winch 41 is employed to apply a posteriorly directed force to the subject at the level of the pelvis by drawing the rope connected to the pelvic traction belt 100 through its associated pulley assembly 44 and onto the winch 41 to thereby firmly position the subject's pelvis against the pelvic pad 19 of the pelvic rest 22. Tension is applied to the dorsolumbar traction belt 102 in the same fashion, by way of its corresponding pulley assembly 44 and winch 40 mounted on the vertical column 16 to apply an anteriorly directed force to the dorsolumbar spine. Tension is applied to the shoulder harness 104 to direct force posteriorly into the shoulders simply by drawing its rope throgh its associated cam-cleat assembly 42 and locking it in place. Tension is applied in like fashion to the cervical fulcrum 106 to direct force anteriorly into the cervical spine, the occipital sling 105 to direct force superiorly into the occiput, and the head halter 108 to apply a posteriorly directed force to the head, all of which have corresponding cam-cleat assemblies 42.

Toprail 24 is constructed to be similar to vertical columns 16, 18 to provide a separation between two opposed flanged members. Two toprail hook assemblies 54 are arranged for travel along the length of the toprail 24 and for being locked in place. Each of the toprail hook assemblies 54 comprises a block like that associated with the cam-cleat assemblies 42 and the pulley assemblies 44 that is machined to travel along the horizontal track within toprail 24 and a J-hook projecting through the block toward the inferior aspect. A fender washer and wingnut are threaded onto the J-hook. The block may be locked into place anywhere along the toprail 24 by simply using the wingnut to tighten the fender washer against the flanges of toprail 24. The toprail hook assemblies 54 can be used in concert with corresponding cam-cleat assemblies 42 to vary the angle of incidence of the forces applied through either the cervical fulcrum 106 or the head halter 108, as shown in phantom in FIG. 2 in connection with the head halter 108. In addition, a toprail hook assembly 54 is engaged with use of the occipital sling 105 to direct the rope from above the patient to the corresponding cam-cleat assembly 42 in the vertical column 16 of the frame. A pulley 107 which freely floats along each of the ropes for the cervical fulcrum 106, occipital sling 105, and head halter 108, is simply draped over the J-hook of the associated toprail hook assembly 54 to redirect the rope from a higher angle of incidence at any chosen position along the toprail 24.

The pelvic traction belt 100 may comprise, for example, a padded belt member 100 connected on either side to a cross strut 110 through a quick-release buckle. The cross strut 110 serves two functions. First, it maintains separation of the belt origins for the comfort of the subject. Second, it is made of an elastic material that functions somewhat as a spring to maintain traction force over time, even with stress relaxation. The cross-strut 110 is in turn centrally connected to a rigid O-ring 111 by way of an eye hook 113 that is threaded through the center of the cross strut 110. A rope that is firmly attached to the O-ring 111 is routed through an associated one of the pulley assemblies 44 and onto winch 41.

The dorsolumbar traction belt 102 may be substantially identical in construction to the pelvic traction belt 100. A rope connected thereto is routed through an associated one of the pulley assemblies 44 and onto winch 40. A cross strut 122 of the dorsolumbar traction belt 102 also has the capacity to function as a spring, more so than the cross strut 110 of the pelvic traction belt 100. Threaded onto the ends of the dorsolumbar traction belt 102 are the male portions of two quick-release buckles 93. When in use, these male portions attach to the female portions of the quick-release buckles 93 on either end of the cross strut 122. The female portions are threaded onto a strap 123 that is routed through one end of the cross strut 122, through an O-ring 112 that is held by an eye bolt 113 mounted in the center of the cross strut 122, and through the other end of the cross strut 122 to the female portion of the other one of the quick-release buckles 93. As force is applied to the dorsolumbar traction belt 102, the cross strut 122 becomes bowed toward the subject. As the subject undergoes stress relaxation and displaces forward, the cross strut 122 recoils to its previous position, thereby helping to maintain the force amplitude being applied to the subject.

The shoulder harness 104 comprises two shoulder pads 120 with a common origin at the superior aspect that originates at a small vertically positioned strut 114. The two inferior ends of the shoulder pads 120 terminate in a slide lock 116. Material threaded through the slide lock 116 on either shoulder pad 120 then completes the circuit by attaching to the inferior aspect of the vertical strut 114. The slide lock 116 functions in such a manner that the length of material connecting to the vertical strut 114 can be adjusted and friction-locked, thereby allowing the tension of each shoulder pad to be adjusted independently. The vertical strut 114 is connected to a rigid O-ring by way of an eye hook threaded through the center of the vertical strut 114. A rope that is firmly attached to the O-ring passes backward through an associated one of the cam-cleat assemblies 42 and terminates in a handle located outside vertical column 18. Tension is applied to the shoulder harness 104 by manually drawing the rope through the associated one of the cam-cleat assemblies 42. The same function of elasticity as described above in connection with the cross strut 122 of dorsolumbar traction belt 102 is provided in like manner by the vertical strut 114 of shoulder harness 104.

The cervical fulcrum 106 comprises a rigid curved member 141 covered with padding. The rigid curved member 141 is attached on either end by rope to a cross strut 143, which is in turn attached centrally to a rigid O-ring 115 by way of an eye bolt that is threaded through the center of the cross strut 113. A rope that is firmly attached to the O-ring 115 is routed through one of the floating pulleys 107 and an associated one of the cam-cleat assemblies 42 positioned within vertical column 16. This rope terminates in a handle 145 outside vertical column 16. The same function of elasticity as described above in connection with the cross strut 122 of dorsolumbar traction belt 102 is provided in like manner by the cross strut 113 of cervical fulcrum 106.

The head halter 108 comprises two rope loops 140, one on each side of the subject's head, that are connected by two cloth bands 109 that are sewn around each of the rope loops 140 and that slide freely with respect thereto. Head halter 108 is arranged to be disposable and interchangable to allow for personal use by each subject. Each of the rope loops 140 of the head halter 108 enters a spring clip 118 at each end of a cross strut 146 to removably secure the head halter 108 to cross strut 146. The cross strut 146 is attached centrally to a rigid O-ring by way of an eye bolt that is threaded centrally through the cross strut 146. A rope is attached to the O-ring by way of a small spring 124 and is routed through an associated one of the cam-cleat assemblies 42 within vertical column 18. Spring 124 works to supplement the elasticity function of cross strut 146 that is like the elasticity function described above in connection with cross strut 122 of dorsolumbar traction belt 102 to thereby provide greater comfort for the subject and to maintain traction force with stress relaxation. Head halter 108 may be positioned on the subject by placing it over the forehead and under the chin or, alternatively, by placing it under the chin and under the occiput.

An occipital sling 105 is identical in construction to the head halter 108 with the exception that one of the cloth bands 109 of head halter 108 is removed. The occipital sling 105 is placed underneath the occiput from above under adequate tension to unweight the head and alleviate compression of the occipito-basilar region. Its rope is routed through a one of the floating pulleys 107 draped over a toprail hook assembly 54 and an associated one of the cam-cleat assemblies 42 within the vertical column 16 of the frame.

I claim:

1. A traction apparatus for selectively applying traction forces to the spine of a human subject, the traction apparatus comprising:

a frame having a base member, front and rear vertical columns attached to front and rear ends, respectively, of the base member, and a horizontal toprail member attached to top ends of the front and rear vertical columns;

a knee rest positioned within the frame for receiving the knees of the subject;

a pelvic rest positioned within the frame rearward of the knee rest for receiving the pelvis of the subject;

pelvic traction means including a pelvic belt adapted for positioning around the front of the subject in the area of the pelvis, the pelvic traction means further including pelvic tensioning means coupled to the pelvic belt and the rear vertical column for adjustably applying a rearward force on the pelvic belt;

dorsolumbar traction means including a dorsolumbar belt adapted for positioning around the rear of the subject in the area of the dorsolumbar spine, the dorsolumbar traction means further including dorsolumbar tensioning means coupled to the dorsolumbar belt and the front vertical column for adjustably applying a forward force on the dorsolumbar belt; and shoulder traction means including a shoulder harness adapted for positioning around each of the shoulders of the subject, the shoulder traction means further including shoulder tensioning means coupled to the shoulder harness and the rear vertical column for adjustably applying a rearward force on the shoulder harness.

2. A traction apparatus as in claim 1, further comprising:

cervical traction means including a cervical fulcrum adapted for positioning around the neck of the subject, the cervical traction means further including cervical tensioning means coupled to the cervical fulcrum and a selected one of the front vertical column and horizontal toprail for adjustably applying a generally forward force on the cervical fulcrum.

3. A traction apparatus as in claim 1, further comprising:

head halter means including a pair of head bands, one of which is adapted for positioning around the chin of the subject and the other of which is adapted for positioning around the forehead of the subject, the head halter means further including head tensioning means coupled to the pair of head bands and the rear column for adjustably applying a generally rearward force on the pair of head bands.

4. A traction apparatus as in claim 1, further comprising:

head halter means including a pair of head bands, one of which is adapted for positioning around the chin of the subject and the other of which is adapted for positioning around the forehead of the subject, the head halter means further including head tensioning means coupled to the pair of head bands and the horizontal toprail member for adjustably applying a generally upward force on the pair of head bands.

5. A traction apparatus as in claim 1, further comprising:

head halter means including a pair of head bands, one of which is adapted for positioning around the chin of the subject and the other of which is adapted for positioning under the occiput of the subject, the head halter means further including head tensioning means coupled to the pair of head bands and the horizontal toprail member for adjustably applying a generally upward force on the pair of head bands.

6. A traction apparatus as in claim 1, further comprising:

head halter means including a pair of head bands, one of which is adapted for positioning around the chin of the subject and the other of which is adapted for positioning around the occiput of the subject, the head halter means further including head tensioning means coupled to the pair of head bands and the rear column for adjustably applying a generally rearward force on the pair of head bands.

7. A traction apparatus as in claim 1, further comprising:

occipital traction means including an occipital sling for positioning under the occiput of the subject, the occipital traction means further including occipital tensioning means coupled to the occipital sling and the and the horizontal toprail member for adjustably applying a generally forward and upward force on the occipital sling.

8. A method for selectively applying traction forces to the spine of a human subject, the method comprising the steps of:

providing pelvic traction means including a pelvic belt adapted for positioning around the front of the subject in the area of the pelvis, the pelvic traction means further including pelvic tensioning means for adjustably applying a rearward force on the pelvic belt;

providing dorsolumbar traction means including a dorsolumbar belt adapted for positioning around the rear of the subject in the area of the dorsolumbar spine, the dorsolumbar traction means further including dorsolumbar tensioning means coupled to the dorsolumbar belt for adjustably applying a forward force on the dorsolumbar belt; and providing shoulder traction means including a shoulder harness adapted for positioning around each of the shoulders of the subject, the shoulder traction means further including shoulder tensioning means coupled to the shoulder harness for adjustably applying a rearward force on the shoulder harness.

9. A method as in claim 8, further comprising the step of providing cervical traction means including a cervical fulcrum adapted for positioning around the neck of the subject, the cervical traction means further including cervical tensioning means coupled to the cervical fulcrum for adjustably applying a generally forward force on the cervical fulcrum.

10. A method as in claim 8, further comprising the step of providing head halter means including a pair of head bands, one of which is adapted for positioning around the chin of the subject and the other of which is adapted for positioning around the forehead of the subject, the head halter means further including head tensioning means coupled to the pair of head bands for adjustably applying a generally rearward force on the pair of head bands.

11. A method as in claim 8, further comprising the step of providing head halter means including a pair of head bands, one of which is adapted for positioning around the chin of the subject and the other of which is adapted for positioning around the forehead of the subject, the head halter means further including head tensioning means coupled to the pair of head bands for adjustably applying a generally upward force on the pair of head bands.

12. A method as in claim 8, further comprising the step of providing head halter means including a pair of head bands, one of which is adapted for positioning around the chin of the subject and the other of which is adapted for positioning under the occiput of the subject, the head halter means further including head tensioning means coupled to the pair of head bands for adjustably applying a generally upward force on the pair of head bands.

13. A method as in claim 8, further comprising the step of providing head halter means including a pair of head bands, one of which is adapted for positioning around the chin of the subject and the other of which is adapted for positioning around the occiput of the subject, the head halter means further including head tensioning means coupled to the pair of head bands for adjustably applying a generally rearward force on the pair of head bands.

14. A method as in claim 8, further comprising the step of providing occipital traction means including an occipital sling for positioning under the occiput of the subject, the occipital traction means further including occipital tensioning means coupled to the occipital sling for adjustably applying a generally upward force on the occipital sling.

\* \* \* \* \*